United States Patent [19]

Obata et al.

[11] Patent Number: 5,280,025

[45] Date of Patent: Jan. 18, 1994

[54] ARALKYLAMINOPYRIMIDINE DERIVATIVE, AND CHEMICAL FOR CONTROLLING NOXIOUS ORGANISMS CONTAINING THE SAME

[75] Inventors: Tokio Obata; Katsutoshi Fujii; Kiyoshi Tsutsumiuchi; Yasushi Nakamoto, all of Ube, Japan

[73] Assignee: Ube Industries, Ltd., Yamaguchi, Japan

[21] Appl. No.: 977,753

[22] Filed: Nov. 17, 1992

[30] Foreign Application Priority Data

Nov. 22, 1991 [JP] Japan .................. 3-354223

[51] Int. Cl.$^5$ .................. C07D 239/42; A01N 43/54
[52] U.S. Cl. .................. 514/256; 544/326; 544/327; 544/329
[58] Field of Search .................. 514/256; 544/326, 327, 544/329

[56] References Cited

FOREIGN PATENT DOCUMENTS

0470600A1 2/1992 European Pat. Off. .

OTHER PUBLICATIONS

Yoshioka et al, Chemical Abstracts, vol. 109, entry 68866m (1988).

*Primary Examiner*—John M. Ford
*Attorney, Agent, or Firm*—Finnegan, Henderson, Farabow, Garrett & Dunner

[57] ABSTRACT

Disclosed are an aralkylaminopyrimidine compound represented by the following formula:

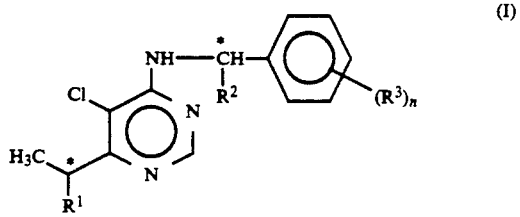

wherein $R^1$ represents a halogen atom, a lower acyloxy group, a hydroxyl group, a lower alkoxy group or a lower alkylthio group; $R^2$ represents a lower alkyl group, a hydrogen atom or a cycloalkyl group; $R^3$ may be the same or different and represents a lower haloalkoxy group, a hydrogen atom, a lower alkyl group, a lower alkoxy group, a halogen atom, a lower alkylthio group, a nitro group, a lower haloalkyl group, a lower alkylsulfinyl group, a lower alkylsulfonyl group, a lower haloalkylthio group or a hydroxyl group; a carbon atom to which * is attached represents an asymmetric carbon atom provided that the case where $R^2$ is a hydrogen atom is excluded; and n represents an integer of 1 to 5.

a method for preparing the same and a chemical for controlling noxious organisms which contains the same as an active ingredient.

8 Claims, No Drawings

ARALKYLAMINOPYRIMIDINE DERIVATIVE, AND CHEMICAL FOR CONTROLLING NOXIOUS ORGANISMS CONTAINING THE SAME

BACKGROUND OF THE INVENTION

This invention relates to a novel aralkylaminopyrimidine derivative which is useful as an insecticide, an acaricide, a nematocide and a fungicide.

The aralkylaminopyrimidine derivative of the present invention is a novel compound so that its activity of controlling noxious organisms has not been known.

In European Patent Publication No. 470 600 (corresponding to Japanese Provisional Patent Publication No. 230670/-1992), there has been disclosed a naphthylalkylaminopyrimidine derivative in which 1-position of an ethyl group at 6-position of a pyrimidine ring is substituted (e.g. Compounds No. 1.197 to 1.202). However, synthesized compounds are only Compounds No. 1.197, No. 1.200 and No. 1.202, and a substituent at 4-position is limited to a naphthylalkylamino group. Further, in these compounds, almost no activity as an agricultural chemical is obtained as mentioned in Example 3 on pages 64 to 74 below.

SUMMARY OF THE INVENTION

An object of the present invention is to provide a novel aralkylaminopyrimidine derivative, a method for preparing the same and a chemical for controlling noxious organisms useful as an insecticide, an acaricide, a nematocide and a fungicide which contains the same derivative as an active ingredient.

The present inventors have studied in order to solve the above task, and consequently found that a novel aralkylaminopyrimidine derivative has remarkable controlling activity as a chemical for controlling noxious organisms useful as an insecticide, an acaricide, a nematocide and a fungicide, to accomplish the present invention.

That is, a first invention is concerned to an aralkylaminopyrimidine derivative represented by the following formula:

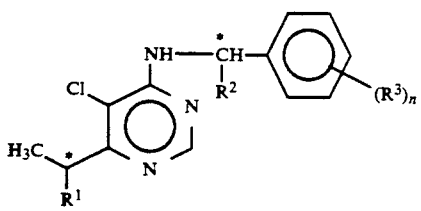

(I)

wherein $R^1$ represents a halogen atom, a lower acyloxy group, a hydroxyl group, a lower alkoxy group or a lower alkylthio group; $R^2$ represents a lower alkyl group, a hydrogen atom or a cycloalkyl group; $R^3$ may be the same or different and represents a lower haloalkoxy group, a hydrogen atom, a lower alkyl group, a lower alkoxy group, a halogen atom, a lower alkylthio group, a nitro group, a lower haloalkyl group, a lower alkylsulfinyl group, a lower alkylsulfonyl group, a lower haloalkylthio group or a hydroxyl group; a carbon atom to which * is attached represents an asymmetric carbon atom provided that the case where $R^2$ is a hydrogen atom is excluded; and n represents an integer of 1 to 5.

In the present invention, the respective optical isomers, racemic compounds and diastereomer compounds of the compound (I) and a mixture of them are also included.

A second invention is concerned to a method for preparing the aralkylaminopyrimidine derivative represented by the above formula (I), which comprises reacting a pyrimidine derivative represented by the following formula:

(II)

wherein $R^1$ has the same meaning as defined above; and

X represents a halogen atom, with an aralkylamine represented by the following formula:

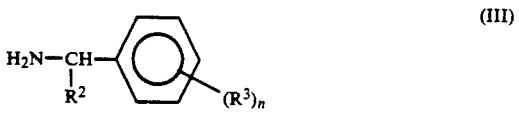

(III)

wherein $R^2$, $R^3$ and n each have the same meanings as defined above.

A third invention is concerned to a chemical for controlling noxious organisms comprising the aralkylaminopyrimidine derivative represented by the above formula (I) as an active ingredient.

DESCRIPTION OF THE PREFERRED EMBODIMENTS

In the following, the present invention is explained in detail.

The characteristic feature of the present invention is an aralkylaminopyrimidine derivative in which 1-position of an ethyl group at 6-position of a pyrimidine ring is substituted by a substituent (e.g. a halogen atom, a lower acyloxy group, a hydroxyl group, a lower alkoxy group or a lower alkylthio group).

In the above novel aralkylaminopyrimidine derivative (I) (including the compounds (I-1), (I-2), (I-3), (I-4) and (I-5) shown below) which is the desired compound, and the above compounds (II) and (III) and the compounds (IV) to (VIII) shown below which are starting materials thereof, $R^1$, $R^2$, $R^3$, $R^4$, $R^5$, $R^6$, X, Y, M and n are as described below.

As $R^1$, there may be mentioned a halogen atom, a lower acyloxy group, a hydroxyl group, a lower alkoxy group and a lower alkylthio group.

As the halogen atom represented by $R^1$, there may be mentioned, for example, a chlorine atom, an iodine atom, a bromine atom and a fluorine atom, preferably a chlorine atom, a fluorine atom and a bromine atom.

As the lower acyloxy group represented by $R^1$, there may be mentioned, for example, those having 2 to 6 carbon atoms in total substituted by a straight or branched alkyl group, preferably those having 2 to 4 carbon atoms in total (e.g. an acetyloxy group, an n-propionyloxy group, an i-propionyloxy group, an n-butyroyloxy group, an i-butyroyloxy group and a t- butyroyloxy group), more preferably an acetyloxy group and a propionyloxy group.

As the lower alkoxy group represented by $R^1$, there may be mentioned, for example, a straight or branched lower alkoxy group having 1 to 6 carbon atoms, preferably those having 1 to 4 carbon atoms (e.g. a methoxy group, an ethoxy group, an n-propoxy group, an i-propoxy group, an n-butoxy group, an i-butoxy group and a t-butoxy group), more preferably a methoxy group.

As the lower alkylthio group represented by $R^1$, there may be mentioned, for example, a straight or branched lower alkylthio group having 1 to 6 carbon atoms, preferably those having 1 to 4 carbon atoms (e.g. a methylthio group, an ethylthio group, an n-propylthio group, an i-propylthio group, an n-butylthio group, an i-butylthio group and a t-butylthio group), more preferably a methylthio group.

As $R^2$, there may be mentioned a lower alkyl group, a hydrogen atom and a lower cycloalkyl group.

As the lower alkyl group represented by $R^2$, there may be mentioned, for example, a straight or branched lower alkyl group having 1 to 6 carbon atoms, preferably those having 1 to 4 carbon atoms (e.g. a methyl group, an ethyl group, an n-propyl group, an i-propyl group, an n-butyl group, an i-butyl group and a t-butyl group), more preferably a methyl group, an ethyl group and an n-propyl group.

As the cycloalkyl group represented by $R^2$, there may be mentioned, for example, those having 3 to 8 carbon atoms, preferably those having 3 to 6 carbon atoms (e.g. a cyclopropyl group, a cyclobutyl group, a cyclopentyl group and a cyclohexyl group), more preferably a cyclopropyl group.

As $R^3$, there may be mentioned a lower haloalkoxy group, a hydrogen atom, a lower alkyl group, a lower alkoxy group, a halogen atom, a lower alkylthio group, a nitro group, a lower haloalkyl group, a lower alkylsulfinyl group, a lower alkylsulfonyl group, a lower haloalkylthio group and a hydroxyl group.

As the lower haloalkoxy group represented by $R^3$, there may be mentioned, for example, a straight or branched lower haloalkoxy group having 1 to 6 carbon atoms, preferably those having 1 to 4 carbon atoms (e.g. a difluoromethoxy group, a trifluoromethoxy group, a bromodifluoromethoxy group, a 2-fluoroethoxy group, a 2-chloroethoxy group, a 2,2,2-trifluoroethoxy group and a 3,3,3-trifluoropropyloxy group), more preferably a difluoromethoxy group and a trifluoromethoxy group.

When $R^3$ is a lower haloalkoxy group, n is an integer of 1 to 5, preferably 1, and the position of the substituent is not particularly limited, but it is preferably 3-position or 4-position.

When $R^3$ is a lower haloalkoxy group and a halogen atom, n is an integer of 2 to 5, preferably 2, and the positions of the substituents are not particularly limited, but they are preferably 3-position and 4-position, more preferably the lower haloalkoxy group is at 4-position and the halogen atom is at 3-position.

When $R^3$ is a lower haloalkoxy group and a lower alkoxy group, n is an integer of 2 to 5, preferably 2, and the positions of the substituents are not particularly limited, but they are preferably 3-position and 4-position, more preferably the lower haloalkoxy group is at 4-position and the lower alkoxy group is at 3-position.

When $R^3$ is a lower haloalkoxy group and a lower alkyl group, n is an integer of 2 to 5, preferably 2 to 4, more preferably 3, and the positions of the substituents are not particularly limited, but they are preferably 3-position, 4-position and 5-position, more preferably the lower haloalkoxy group is at 4-position and the lower alkyl groups are at 3-position and 5-position.

When $R^3$ is a hydrogen atom, n represents 5.

As the lower alkyl group represented by $R^3$, there may be mentioned, for example, a straight or branched lower alkyl group having 1 to 6 carbon atoms, preferably those having 1 to 4 carbon atoms (e.g. the lower alkyl group described above as $R^2$), more preferably a methyl group and a t-butyl group.

When $R^3$ is a lower alkyl group, n is an integer of 1 to 5, preferably 1 or 2, and the position of the substituent is not particularly limited, but it is preferably 2-position, 3-position, 4-position and 5-position, more preferably 2-position or 3-position when n is 1 and 3-position and 4-position or 2-position and 5-position when n is 2.

As the lower alkoxy group represented by $R^3$, there may be mentioned, for example, a straight or branched lower alkoxy group having 1 to 6 carbon atoms, preferably those having 1 to 4 carbon atoms (e.g. the lower alkoxy group described above as $R^1$), more preferably a methoxy group.

When $R^3$ is a lower alkoxy group, n is an integer of 1 to 5, preferably 1, and the position of the substituent is not particularly limited, but it is preferably 4-position.

As the halogen atom represented by $R^3$, there may be mentioned, for example, the halogen atom described above as $R^1$, preferably a chlorine atom, a fluorine atom and a bromine atom.

When $R^3$ is a halogen atom, n is an integer of 1 to 5, preferably 1 to 4, more preferably 1 or 2, and the position of the substituent is not particularly limited, but it is preferably 2-position, 3-position or 4-position when $R^3$ is a chlorine atom, 2-position, 3-position, 4-position or 6-position when $R^3$ is a fluorine atom, and 2-position or 4-position when $R^3$ is a bromine atom.

As the lower alkylthio group represented by $R^3$, there may be mentioned, for example, a straight or branched lower alkylthio group having 1 to 6 carbon atoms, preferably those having 1 to 4 carbon atoms (e.g. the lower alkylthio group described as $R^1$), more preferably a methylthio group, an ethylthio group, an n-propylthio group and an n-butylthio group, most preferably a methylthio group.

When $R^3$ is a lower alkylthio group, n is an integer of 1 to 5, preferably 1, and the position of the substituent is not particularly limited, but it is preferably 4-position.

As the lower haloalkylthio group represented by $R^3$, there may be mentioned, for example, those substituted by the halogen atom described above as $R^1$ and a straight or branched alkyl group having 1 to 6 carbon atoms, preferably those substituted by a fluorine atom as a halogen atom and an alkyl group having 1 to 4 carbon atoms (e.g. a difluoromethylthio group, a trifluoromethylthio group, a bromodifluoromethylthio group, a 2-fluoroethylthio group, a 2,2,2-trifluoroethylthio group and a 3,3,3-trifluoropropylthio group), more preferably a difluoromethylthio group.

When $R^3$ is a lower haloalkylthio group, n is an integer of 1 to 5, preferably 1, and the position of the substituent is not particularly limited, but it is preferably 4-position.

When $R^3$ is a nitro group, n is an integer of 1 to 5, preferably 1, and the position of the substituent is not particularly limited, but it is preferably 4-position.

As the lower haloalkyl group represented by $R^3$, there may be mentioned, for example, a straight or branched lower haloalkyl group having 1 to 6 carbon atoms, preferably those having 1 to 4 carbon atoms (e.g. a trifluoromethyl group, a 2-fluoroethyl group and a 2,2,2-trifluoroethyl group), more preferably a trifluoromethyl group.

When $R^3$ is a lower haloalkyl group, n is an integer of 1 to 5, preferably 1, and the position of the substituent is not particularly limited, but it is preferably 2-position or 3-position.

As the lower alkylsulfinyl group represented by $R^3$, there may be mentioned, for example, a straight or branched lower alkylsulfinyl group having 1 to 6 carbon atoms, preferably those having 1 to 4 carbon atoms (e.g. a methylsulfinyl group, an ethylsulfinyl group, an n-propylsulfinyl group, an i-propylsulfinyl group, an n-butylsulfinyl group, an i-butylsulfinyl group, a sec-butylsulfinyl group and a t-butylsulfinyl group), more preferably a methylsulfinyl group, an ethylsulfinyl group, an n-propylsulfinyl group and an n-butylsulfinyl group.

When $R^3$ is a lower alkylsulfinyl group, n is an integer of 1 to 5, preferably 1, and the position of the substituent is not particularly limited, but it is preferably 4-position.

As the lower alkylsulfonyl group represented by $R^3$, there may be mentioned, for example, a straight or branched lower alkylsulfonyl group having 1 to 6 carbon atoms, preferably those having 1 to 4 carbon atoms (e.g. a methylsulfonyl group, an ethylsulfonyl group, an n-propylsulfonyl group, an i-propylsulfonyl group, an n-butylsulfonyl group, an i-butylsulfonyl group, a sec-butylsulfonyl group and a t-butylsulfonyl group), more preferably a methylsulfonyl group, an ethylsulfonyl group, an n-propylsulfonyl group and an n-butylsulfonyl group.

When $R^3$ is a lower alkylsulfonyl group, n is an integer of 1 to 5, preferably 1, and the position of the substituent is not particularly limited, but it is preferably 4-position.

When $R^3$ is a hydroxyl group, n is an integer of 1 to 5, preferably 1, and the position of the substituent is not particularly limited, but it is preferably 4-position.

$R^4$ and X each represent a halogen atom (e.g. the halogen atom described above as $R^1$).

M represents an alkali metal.

$R^5$ represents a lower acyloxy group (lower aliphatic carboxylic acid residue) corresponding to $R^1$.

In $R^6$-Y, $R^6$ represents a lower alkyl group corresponding to $R^1$, and Y represents an oxygen atom or a sulfur atom. That is, $R^6$-Y represents a lower alkoxy group or a lower alkylthio group corresponding to $R^1$.

The compound (I) of the present invention has an amino group and can form an acid addition salt easily. Such a salt is also included in the present invention.

As an acid for forming an acid addition salt, there may be mentioned, for example, inorganic acids (e.g. hydrochloric acid, hydrobromic acid, nitric acid, sulfuric acid and phosphoric acid), carboxylic acids (e.g. formic acid, oxalic acid, fumaric acid, adipic acid, stearic acid, oleic acid and aconitic acid), organic sulfonic acids (e.g. methanesulfonic acid, benzenesulfonic acid and p-toluenesulfonic acid) and saccharin.

Specific examples of the compound (I) of the present invention are shown in Table 1, and physical properties of Compounds 4, 10, 103, 111 and 122 are shown in Table 2.

TABLE 1

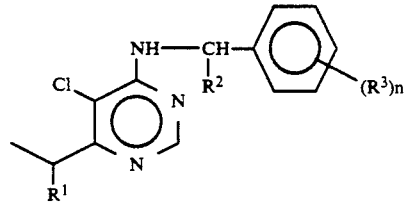

(I)

| Compound | $R^1$ | $R^2$ | $(R^3)n$ | Physical properties |
|---|---|---|---|---|
| 1 | Cl | $CH_3$ | 4-$OCHF_2$ | $n_D^{26.1}$ 1.5571 |
| 2 | —$OCOCH_3$ | " | " | $n_D^{25.5}$ 1.3972 |
| 3 | OH | " | " | $n_D^{26.2}$ 1.5584 |
| 4 | F | " | " | shown in Table 2 |
| 5 | Br | " | " | |
| 6 | —$OCH_3$ | " | " | |
| 7 | —$SCH_3$ | " | " | |
| 8 | Cl | $C_2H_5$ | " | $n_D^{26.1}$ 1.5481 |
| 9 | —$OCOCH_3$ | $C_2H_5$ | 4-$OCHF_2$ | $n_D^{24.9}$ 1.5414 |
| 10 | OH | " | " | shown in Table 2 |
| 11 | F | " | " | $n_D^{24.5}$ 1.5408 |
| 12 | Br | " | " | |
| 13 | —$OCH_3$ | " | " | |
| 14 | —$SCH_3$ | " | " | |
| 15 | Cl | $CH_3$ | H | $n_D^{24.6}$ 1.5894 |
| 16 | —$OCOCH_3$ | " | " | $n_D^{25.1}$ 1.5628 |
| 17 | —$OCOC_2H_5$ | $CH_3$ | H | |
| 18 | OH | " | " | $n_D^{24.1}$ 1.5794 |
| 19 | F | " | " | $n_D^{21.8}$ 1.5725 |
| 20 | Br | " | " | |
| 21 | —$OCH_3$ | " | " | $n_D^{24.7}$ 1.5692 |
| 22 | —$SCH_3$ | " | " | $n_D^{24.4}$ 1.6010 |
| 23 | Cl | $C_2H_5$ | " | $n_D^{24.6}$ 1.5809 |
| 24 | " | n-$C_3H_7$ | " | $n_D^{24.9}$ 1.5726 |
| 25 | Cl | H | 4-t-$C_4H_9$ | m.p. |

TABLE 1-continued (I)

$$\text{structure: 5-chloro-6-(CHR}^1\text{-CH}_3\text{)-pyrimidin-4-yl-NH-CHR}^2\text{-C}_6\text{H}_4\text{-(R}^3)_n$$

| Compound | R¹ | R² | (R³)n | Physical properties |
|---|---|---|---|---|
| 26 | " | " | 4-OCH₃ | 110~112° C. m.p. |
| 27 | " | " | 4-F | 85~86° C. m.p. |
| 28 | " | " | 4-CH₃ | 87~88.5° C. m.p. |
| 29 | " | " | 2, 4-Cl₂ | 83~85° C. m.p. |
| 30 | " | " | 3, 4-Cl₂ | 135~136° C. m.p. |
| 31 | " | " | 4-Br | 106~107° C. m.p. |
| 32 | " | " | 4-NO₂ | 98~100° C. m.p. |
| 33 | Cl | C₂H₅ | 4-Cl | 113~115° C. |
| 34 | " | " | 4-CH₃ | $n_D^{18.4}$ 1.5924 |
| 35 | " | CH₃ | 3-CH₃ | $n_D^{23.0}$ 1.5692 |
| 36 | " | H | H | $n_D^{23.1}$ 1.5780 |
| 37 | " | " | 4-Cl | m.p. 112~114° C. |
| 38 | " | " | 2-CF₃ | m.p. 85~86.5° C. |
| 39 | —OCOCH₃ | " | H | 97~98° C. |
| 40 | " | " | 4-Cl | $n_D^{20.6}$ 1.5674 |
| 41 | Cl | H | 2-Cl | $n_D^{20.6}$ 1.5723 |
| 42 | " | " | 2-F | m.p. 132~133° C. |
| 43 | " | " | 3-F | m.p. 118~120° C. |
| 44 | " | " | 2, 6-F₂ | m.p. 100~101° C. |
| 45 | " | " | 2-Br | m.p. 114.5~115.5° C. |
| 46 | OH | " | H | m.p. 113~115° C. |
| 47 | " | " | 4-Cl | m.p. 92~93° C. |
| 48 | F | " | H | m.p. 101~102° C. |
| 49 | F | H | 4-Cl | m.p. 78~79° C. |
| 50 | —OCOCH₃ | " | 4-CH₃ | m.p. 106~107° C. |
| 51 | " | " | 4-OCH₃ | $n_D^{23.5}$ 1.5604 |
| 52 | OH | " | 4-CH₃ | $n_D^{22.2}$ 1.5650 |
| 53 | " | " | 4-OCH₃ | m.p. 106~108° C. |
| 54 | F | " | 4-CH₃ | m.p. 61~64° C. |
| 55 | " | " | 4-OCH₃ | m.p. 96~97° C. |
| 56 | Cl | CH₃ | " | 117~118° C. |
| 57 | —OCOCH₃ | CH₃ | 4-OCH₃ | $n_D^{24.8}$ 1.5937 |
| 58 | OH | " | " | $n_D^{17.5}$ 1.5692 |
| 59 | F | " | " | $n_D^{24.4}$ 1.5777 |
| 60 | Cl | " | 4-Cl | $n_D^{24.9}$ 1.5754 |
| 61 | OH | " | " | |
| 62 | F | " | " | |
| 63 | OH | C₂H₅ | H | m.p. 61~63° C. |
| 64 | F | " | " | $n_D^{23.3}$ 1.5658 |
| 65 | Cl | CH₃ | 4-Br | $n_D^{26.2}$ 1.5935 |
| 66 | —OCOCH₃ | " | " | $n_D^{25.3}$ 1.5794 |
| 67 | OH | " | " | m.p. 116~120° C. |
| 68 | —OCOCH₃ | C₂H₅ | 4-CH₃ | $n_D^{23.7}$ 1.5614 |

TABLE 1-continued

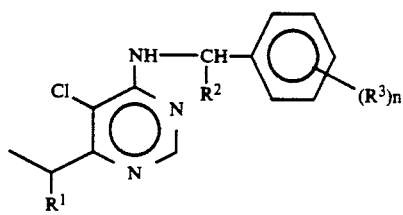

(I)

| Compound | $R^1$ | $R^2$ | $(R^3)n$ | Physical properties |
|---|---|---|---|---|
| 69 | OH | " | " | m.p. 98~101° C. |
| 70 | F | " | " | $n_D^{23.6}$ 1.5630 |
| 71 | " | CH$_3$ | 4-Br | $n_D^{17.8}$ 1.5943 |
| 72 | Cl | " | 3-CF$_3$ | $n_D^{24.8}$ 1.5694 |
| 73 | —OCOCH$_3$ | CH$_3$ | 3-CF$_3$ | $n_D^{25.6}$ 1.5445 |
| 74 | OH | " | " | $n_D^{14.0}$ 1.5635 |
| 75 | F | " | " | $n_D^{24.3}$ 1.5386 |
| 76 | Cl | C$_2$H$_5$ | 4-F | $n_D^{22.8}$ 1.5625 |
| 77 | —OCOCH$_3$ | " | " | $n_D^{24.0}$ 1.5452 |
| 78 | OH | " | " | m.p. 80~83° C. |
| 79 | F | " | " | $n_D^{25.0}$ 1.5423 |
| 80 | Cl |  | 4-Cl | $n_D^{19.2}$ 1.6027 |
| 81 | —OCOC$_2$H$_5$ |  | 4-Cl |  |
| 82 | OH | " | " |  |
| 83 | F | " | " | $n_D^{18.1}$ 1.5920 |
| 84 | Cl | CH$_3$ | 4-OCF$_3$ | $n_D^{20.4}$ 1.5442 |
| 85 | " | " | " | $n_D^{20.4}$ 1.5403 |
| 86 | —OCOCH$_3$ | " | " | $n_D^{25.5}$ 1.5238 |
| 87 | OH | " | " | m.p. 120~123° C. |
| 88 | F | " | " | $n_D^{23.7}$ 1.5219 |
| 89 | Cl | CH$_3$ | 3-Cl | $n_D^{25.2}$ 1.5595 |
| 90 | " | " | " | $n_D^{25.4}$ 1.4874 |
| 91 | OH | " | " | m.p. 90~93° C. |
| 92 | F | " | " | $n_D^{23.5}$ 1.5772 |
| 93 | Cl | " | 3-Br | $n_D^{23.5}$ 1.6007 |
| 94 | —OCOCH$_3$ | " | " | $n_D^{23.5}$ 1.5784 |
| 95 | OH | " | " | $n_D^{23.6}$ 1.5998 |
| 96 | F | " | " | $n_D^{23.7}$ 1.5862 |
| 97 | Cl | CH$_3$ | 4-SCH$_3$ | $n_D^{22.3}$ 1.6073 |
| 98 | —OCOCH$_3$ | " | " | $n_D^{23.4}$ 1.5950 |
| 99 | OH | " | " | m.p. 94~97° C. |
| 100 | F | " | " | $n_D^{24.2}$ 1.5637 |
| 101 | Cl | " | 4-NO$_2$ | m.p. 104~106° C. |
| 102 | F | " | " | $n_D^{25.5}$ 1.5923 |
| 103 | " | " | 4-SOCH$_3$ | shown in Table 2 |
| 104 | " | " | 4-SO$_2$CH$_3$ | m.p. 153~155° C. |
| 105 | F | CH$_3$ | 4-SCHF$_2$ | $n_D^{24.3}$ 1.5118 |
| 106 | " | " | 3-OCHF$_2$ | $n_D^{21.0}$ 1.5490 |
| 107 | " | " | 3-Cl, 4-OCHF$_2$ | $n_D^{21.1}$ 1.5559 |
| 106 | " | " | 3-OCH$_3$, 4-OCHF$_2$ | $n_D^{21.4}$ 1.5472 |
| 109 | " | " | 3,5-(CH$_3$)$_2$, 4-OCHF$_2$ | $n_D^{24.3}$ 1.5118 |
| 110 | " | " | 3,4-(OCH$_3$)$_2$ | $n_D^{24.4}$ 1.5358 |
| 111 | " | " | 2,5-(OCH$_3$)$_2$ | shown in Table 2 |
| 112 | Cl | " | 4-SCH$_2$CH$_3$ | $n_D^{25.0}$ 1.5507 |
| 113 | —OCOCH$_3$ | CH$_3$ | 4-SCH$_2$CH$_3$ | $n_D^{24.5}$ 1.5872 |
| 114 | OH | " | " | m.p. 58~61° C. |
| 115 | F | " | " | $n_D^{24.4}$ 1.5952 |
| 116 | " | " | 4-SOCH$_2$CH$_3$ | m.p. 81~82° C. |

TABLE 1-continued

| Compound | R¹ | R² | (R³)n | Physical properties |
|---|---|---|---|---|
| 117 | " | " | 4-SO$_2$CH$_2$CH$_3$ | m.p. 112~114° C. |
| 118 | Cl | " | 4-SCH$_2$CH$_2$CH$_3$ | n$_D^{25.9}$ 1.5882 |
| 119 | —OCOCH$_3$ | " | " | n$_D^{24.2}$ 1.5718 |
| 120 | OH | " | 4-SOCH$_2$CH$_2$CH$_3$ | n$_D^{23.5}$ 1.5914 |
| 121 | F | CH$_3$ | 4-SCH$_2$CH$_2$CH$_3$ | n$_D^{26.3}$ 1.5770 |
| 122 | " | " | 4-SOCH$_2$CH$_2$CH$_3$ | shown in Table 2 |
| 123 | " | " | 4-SO$_2$CH$_2$CH$_2$CH$_3$ | m.p. 86~87° C. |
| 124 | Cl | " | 4-SCH$_2$CH$_2$CH$_2$CH$_3$ | n$_D^{25.8}$ 1.5692 |
| 125 | —OCOCH$_3$ | " | " | n$_D^{24.2}$ 1.5697 |
| 126 | OH | " | " | n$_D^{23.4}$ 1.5852 |
| 127 | F | " | " | n$_D^{26.2}$ 1.5738 |
| 128 | " | " | 4-SOCH$_2$CH$_2$CH$_2$CH$_3$ | n$_D^{23.3}$ 1.5836 |
| 129 | F | CH$_3$ | 4-SO$_2$CH$_2$CH$_2$CH$_2$CH$_3$ | n$_D^{23.3}$ 1.5693 |
| 130 | OH | " | 4-OH | m.p. 195~198° C. |
| 131 | F | " | " | m.p. 129~132° C. |
| 132 | Cl | C$_2$H$_5$ | 4-SCH$_3$ | n$_D^{25.1}$ 1.5950 |
| 133 | —OCOCH$_3$ | " | " | n$_D^{21.6}$ 1.5716 |
| 134 | OH | " | " | m.p. 149-151° C. |
| 135 | F | " | " | n$_D^{22.3}$ 1.5856 |
| 136 | " | " | 4-SOCH$_3$ | m.p. 96-99° C. |
| 137 | F | C$_2$H$_5$ | 4-SO$_2$CH$_3$ | m.p. 154-156° C. |
| 138 | Cl | ▷ | 4-SCH$_3$ | n$_D^{22.3}$ 1.5980 |
| 139 | —OCOCH$_3$ | " | " | m.p. 93-95° C. |
| 140 | OH | " | " | m.p. 105-107° C. |
| 141 | F | " | " | n$_D^{25.0}$ 1.5990 |
| 142 | " | " | 4-SOCH$_3$ | m.p. 116-118° C. |
| 143 | " | " | 4-SO$_2$CH$_3$ | m.p. 149-151° C. |

TABLE 2

| Compound | Physical properties: ¹H-NMR(CDCl$_3$)δppm |
|---|---|
| 4 | 2.08~2.18(d-d, 6H), 5.38(m, 1H), 5.68(d, 1H), 5.78(q, 1H), 6.12~6.88(t, 1H), 7.12(d, 2H), 7.37(d, 2H), 8.50(s, 1H) |
| 10 | 0.90~1.00(m, 3H), 1.38~150(t, 3H), 1.84~2.04(m, 2H), 4.92~5.06(m, 1H), 5.06~5.20(q, 1H), 5.65~5.80(d, 1H), 6.10~6.88 (d-t, 1H), 7.05~7.18(m, 2H), 7.25~7.40(m, 2H), 8.43(s, 1H) |
| 103 | 1.55~1.78(m, 6H), 2.72(s, 3H), 5.34~5.50(qui, 1H) 5.68~6.08(m, 2H), 7.46~7.68(m, 4H), 8.50(s, 1H) |
| 111 | 1.52~1.74(m, 6H), 3.76(s, 1H), 3.90(s, 1H), 5.40~5.56(qui, 1H) 5.70~6.05(d-q, 1H), 6.60~6.70(d, 1H), 6.70~6.92(m, 3H), 8.50(s, 1H) |
| 122 | 0.98~1.10(t, 3H), 1.55~1.88(m, 8H), 2.62~2.78(m, 2H), 5.34~5.55(qui, 1H), 5.65~6.08(m, 2H), 7.45~7.65(m, 4H), 8.50(s, 1H) |

As a preferred embodiment of preparing the aralkylaminopyrimidine derivative represented by the above formula (I), there may be mentioned, in addition to Synthesis method 1 described above as the second invention, 5 preparation methods (Synthesis methods 2 to 6) described below.

(Synthesis method 2)

A method for preparing an aralkylaminopyrimidine derivative of the above formula (I) in which R¹ is a lower acyloxy group, which comprises reacting an aralkylaminopyrimidine derivative represented by the following formula:

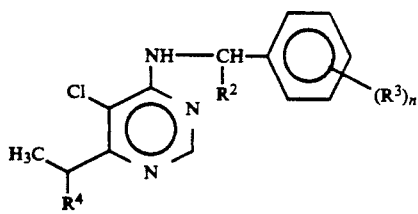
(I-1)

wherein $R^2$, $R^3$ and n each have the same meanings as defined above; and $R^4$ represents a halogen atom, with a lower aliphatic carboxylic acid represented by the following formula:

$$R^5-H \qquad (IV)$$

wherein $R^5$ represents a lower acyloxy group.
(Synthesis method 3)

A method for preparing an aralkylaminopyrimidine derivative of the above formula (I) in which $R^1$ is a hydroxyl group, which comprises reacting an aralkylaminopyrimidine derivative represented by the following formula:

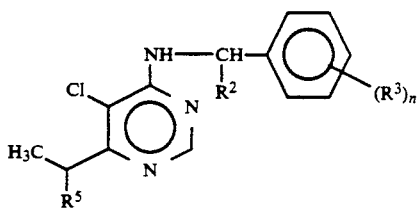
(I-2)

wherein $R^2$, $R^3$, $R^5$ and n each have the same meanings as defined above,
with an inorganic base represented by the following formula:

$$M-OH \qquad (V)$$

wherein M represents an alkali metal.
(Synthesis method 4)

A method for preparing an aralkylaminopyrimidine derivative of the above formula (I) in which $R^1$ is a fluorine atom, which comprises reacting an aralkylaminopyrimidine derivative represented by the following formula:

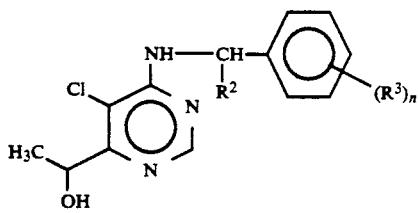
(I-3)

wherein $R^2$, $R^3$ and n each have the same meanings as defined above,
with a fluorinating agent.
(Synthesis method 5)

A method for preparing an aralkylaminopyrimidine derivative of the above formula (I) in which $R^1$ is a lower alkoxy group or a lower alkylthio group, which comprises reacting the aralkylaminopyrimidine derivative represented by the above formula (I-1) with an alcohol or mercaptan represented by the following formula:

$$R^6-Y-H \qquad (VI)$$

wherein $R^6$ represents a lower alkyl group and Y represents an oxygen atom or a sulfur atom.
(Synthesis method 6)

A method for preparing an aralkylaminopyrimidine derivative of the above formula (I) in which $R^1$ is a fluorine atom, which comprises reacting the aralkylaminopyrimidine derivative represented by the above formula (I-1) with an alkali metal fluoride compound represented by the following formula:

$$M-F \qquad (VII)$$

wherein M represents an alkali metal.

The synthesis of the compound (I) of the present invention is described in detail by referring to Synthesis methods 1 to 6.
(Synthesis method 1)

The compound (I) of the present invention can be synthesized generally by reacting the starting compounds (II) and (III) in the presence or absence of a solvent as shown below. In order to accelerate the reaction, the starting compounds are preferably reacted in the presence of a base.

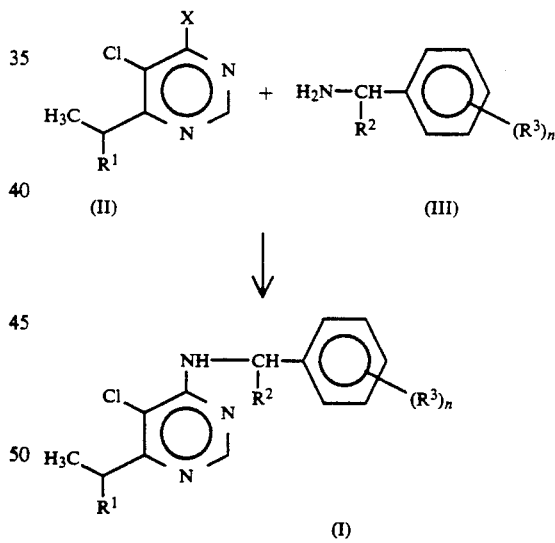

wherein $R^1$, $R^2$, $R^3$, X and n each have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloromethane, dichloroethane, trichloroethylene and cyclohexane; ethers such as diethyl ether, tetrahydrofuran and dioxane; ketones such as acetone and methyl ethyl ketone; amides such as N,N-dimethylformamide and N,N-dimethylacetamide; nitriles such as acetonitrile and propionitrile; organic bases such as triethylamine, pyridine and N,N-dimethylaniline; 1,3-dimethyl-2-imidazolidinone; dimethyl sulfoxide; and a mixture of the above solvents.

The solvent may be used in such an amount that the concentration of the compound (II) becomes 5 to 80% by weight, preferably in such an amount that the concentration of the compound (II) becomes 10 to 70% by weight.

The base is not particularly limited, and may include, for example, organic bases (e.g. triethylamine, pyridine, N,N-dimethylaniline and 1,8-diazabicyclo[5.4.0]-7-undecene (DBU)); alkali metal alkoxides (e.g. sodium methoxide and sodium ethoxide); and inorganic bases (e.g. sodium hydride, sodium amide, sodium hydroxide, potassium hydroxide, sodium carbonate, sodium hydrogen carbonate and potassium carbonate). Preferred are organic bases.

The amount of the base to be used may be 0.001 to 5-fold mole, preferably 0.8 to 5-fold mole based on the amount of the compound (II).

The reaction temperature is not particularly limited, but may be in the temperature range of room temperature to a boiling point or lower of a solvent used, preferably 80° to 110° C.

The reaction time varies depending on the above concentration and temperature, but may be generally 0.3 to 2 hours.

The amount of the starting compound (III) to be used is 0.5 to 2-fold mole, preferably 0.8 to 1.5-fold mole based on the amount of the compound (II).

The compound (II) (when $R^1$ is X) to be used in the present invention can be prepared generally by reacting the starting compounds (VIII-1) and (IX-1) in a solvent as shown below.

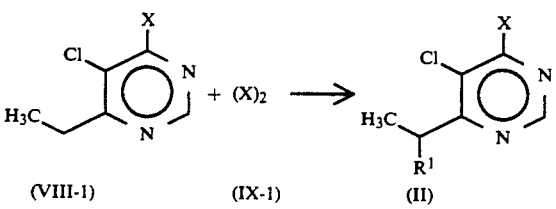

wherein $R^1$ is X; and X has the same meaning as defined above.

As the solvent, there may be mentioned the solvent as described above, and the solvent may be used in such an amount that the concentration of the compound (VIII-1) becomes 5 to 80% by weight.

The reaction temperature is not particularly limited, but may be in the temperature range of room temperature to a boiling point or lower of a solvent used.

The reaction time varies depending on the above concentration and temperature, but may be generally 2 to 10 hours.

The amount of the starting compound (IX-1) to be used is 0.5 to 3-fold mole, preferably 0.5 to 1.7-fold mole based on the amount of the compound (VIII-1).

The compound (VIII-3) can be prepared easily as shown in the following scheme according to, for example, the method described in "Journal of Chemical Society", pp. 3478 to 3481 (1955).

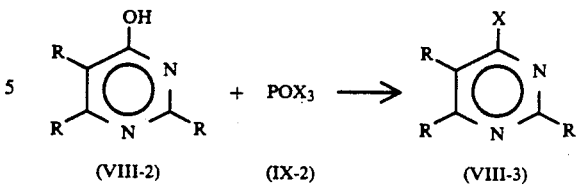

wherein X has the same meaning as defined above; and R each represents a lower alkyl group, a hydrogen atom, a hydroxyl group or a halogen atom as desired.

After completion of the reaction, the desired compound (II) prepared as described above may be subjected to conventional post-treatments such as extraction, condensation and filtration, and purified suitably by a known means such as recrystallization and various chromatographies, if necessary.

As the compound (II), there may be mentioned, for example, the starting compounds (II-1) to (II-7) shown in Table 3.

TABLE 3

(II)

| Compound | X | $R^1$ | Physical properties |
|---|---|---|---|
| II-1 | Cl | Cl | b.p.: 110 to 113° C./7 mmHg |
| II-2 | Br | Br | b.p.: 114 to 116° C./3 mmHg m.p.: 60 to 62° C. |
| II-3 | Cl | Br | b.p.: 93 to 95° C./3 mmHg |
| II-4 | Cl | F | b.p.: 229 to 231° C. |
| II-5 | F | F | b.p.: 192 to 194° C. |
| II-6 | Cl | O—OCCH$_3$ | $n_D^{17.7}$ 1.5222 |
| II-7 | Cl | OH | $n_D^{19.3}$ 1.5540 |

The compound (III) to be used in the present invention can be prepared easily as shown in the following scheme according to, for example, the method described in J. Am. Chem. Soc., Vol. 70, p. 1315 (1948) or Org. Syn., Coll., Vol. 2, p. 505 (1943).

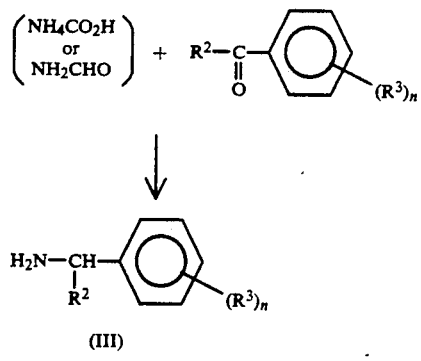

wherein $R^2$, $R^3$ and n each have the same meanings as defined above.

As the compound (III), there may be mentioned, for example, the respective compounds (III) comprising the respective kinds of substituents corresponding to Compounds 1 to 148 shown in Table 1 (referred to as Compounds (III)$_1$ to (III)$_{148}$, and, for example, Compound (III)$_1$ means a compound wherein R$^2$ is a methyl group and (R$^3$)$_n$ is 4—OCHF$_2$ in the compound represented by the formula (III)).

As the compound (I), there may be mentioned, for example, Compounds 1 to 148 shown in Table 1 (Compound 1 means a compound wherein R$^1$ is a chlorine atom, R$^2$ is a methyl group and (R$^3$)$_n$ is 4—OCHF$_2$ in the compound represented by the formula (I)).

(Synthesis method 2)

The compound (I-2) (the compound (I) in which R$^1$ is a lower acyloxy group) can be synthesized generally by reacting the compound (I-1) and the compound (IV) in the presence or absence of a solvent. In order to accelerate the reaction, the compounds are preferably reacted in the presence of a base.

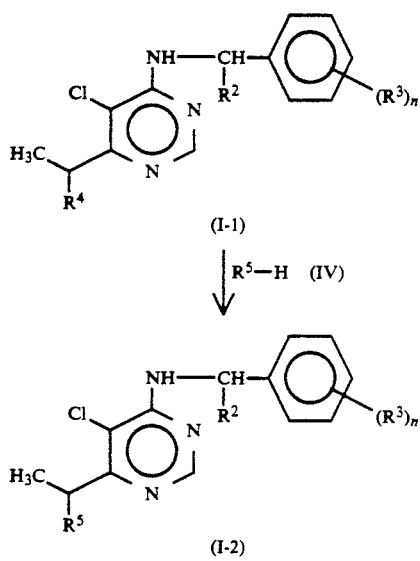

wherein R$^2$, R$^3$, R$^4$, R$^5$ and n each have the same meanings as defined above.

As the solvent, there may be mentioned, in addition to the solvent described in Synthesis method 1, aliphatic carboxylic acids such as acetic acid and propionic acid, and a mixture thereof, and preferred are N,N-dimethylformamide and an aliphatic carboxylic acid which is identical with an acyloxy group to be introduced.

The solvent may be used in such an amount that the concentration of the compound (I-1) becomes 5 to 80% by weight, preferably in such an amount that the concentration of the compound (I-1) becomes 10 to 70% by weight.

As the base, there may be mentioned the base described in Synthesis method 1, and preferred are inorganic bases.

The amount of the base to be used may be 1 to 5-fold mole, preferably 2 to 5-fold mole based on the amount of the compound (I-1).

The reaction temperature is not particularly limited, but may be in the temperature range of room temperature to a boiling point or lower of a solvent used, preferably 80° to 120° C.

The reaction time varies depending on the above concentration and temperature, but may be generally 10 to 50 hours.

As the compound (IV), a commercially available product can be used.

After completion of the reaction, the desired compound (I-2) prepared as described above may be subjected to conventional post-treatments such as extraction, condensation and filtration, and purified suitably by a known means such as recrystallization and various chromatographies, if necessary.

As the compound (I-2), there may be mentioned, for example, the respective compounds (I-2) comprising the respective kinds of substituents corresponding to Compounds 2, 9, 16, 17, 39, 40, 50, 51, 57, 66, 68, 73, 77, 81, 86, 94, 98, 113, 119, 125, 133 and 139 shown in Table 1 (referred to as Compounds (I-2)$_2$, (I-2)$_9$, (I-2)$_{16}$, (I-2)$_{17}$, (I-2)$_{39}$, (I-2)$_{40}$, (I-2)$_{50}$, (I-2)$_{51}$, (I-2)$_{57}$, (I-2)$_{66}$, (I-2)$_{68}$, (I-2)$_{73}$, (I-2)$_{77}$, (I-2)$_{81}$, (I-2)$_{86}$, (I-2)$_{94}$, (I-2)$_{98}$, (I-2)$_{113}$, (I-2)$_{119}$, (I-2)$_{125}$, (I-2)$_{133}$ and (I-2)$_{139}$, and, for example, Compound (I-2)$_2$ means a compound wherein R$^1$ is an acetyloxy group, R$^2$ is a methyl group and (R$^3$)$_n$ is 4—OCHF$_2$ in the compound represented by the formula (I)).

(Synthesis method 3)

The compound (I-3) (the compound (I) in which R$^1$ is a hydroxyl group) can be synthesized generally be reacting the compound (I-2) and the compound (V) in a solvent in the presence of a base.

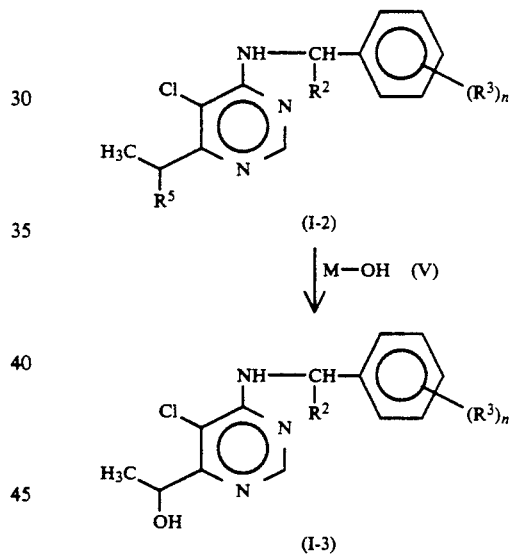

wherein R$^2$, R$^3$, R$^5$, M and n each have the same meanings as defined above.

As the solvent, there may be mentioned, in addition to the ethers, ketones and amides described in Synthesis method 1, alcohols (e.g. methanol, ethanol, propanol and butanol), water and a mixture of the above solvents, and preferred is a mixture of alcohol and water.

The solvent may be used in such an amount that the concentration of the compound (I-2) becomes 5 to 80% by weight, preferably in such an amount that the concentration of the compound (I-2) becomes 10 to 70% by weight.

As the base, there may be mentioned the inorganic base described in Synthesis method 1, and preferred are sodium hydroxide and potassium hydroxide.

The amount of the base to be used may be 1 to 5-fold mole, preferably 2 to 5-fold mole based on the amount of the compound (I-2).

The reaction temperature is not particularly limited, but may be in the temperature range of room temperature to a boiling point or lower of a solvent used, preferably room temperature to 50° C.

The reaction time varies depending on the above concentration and temperature, but may be generally 0.5 to 1 hour.

As the compound (V), a commercially available product can be used.

After completion of the reaction, the desired compound (I-3) prepared as described above may be subjected to conventional post-treatments such as extraction, condensation and filtration, and purified suitably by a known means such as recrystallization and various chromatographies, if necessary.

As the compound (I-3), there may be mentioned, for example, the respective compounds (I-3) comprising the respective kinds of substituents corresponding to Compounds 3, 10, 18, 46, 47, 52, 53, 58, 61, 63, 67, 69, 74, 78, 82, 87, 91, 95, 99, 114, 120, 126, 130, 134 and 140 shown in Table 1 (referred to as Compounds $(I-3)_3$, $(I-3)_{10}$, $(I-3)_{18}$, $(I-3)_{46}$, $(I-3)_{47}$, $(I-3)_{52}$, $(I-3)_{53}$, $(I-3)_{58}$, $(I-3)_{61}$, $(I-3)_{63}$, $(I-3)_{67}$, $(I-3)_{69}$, $(I-3)_{74}$, $(I-3)_{78}$, $(I-3)_{82}$, $(I-3)_{87}$, $(I-3)_{91}$, $(I-3)_{95}$, $(I-3)_{99}$, $(I-3)_{114}$, $(I-3)_{120}$, $(I-3)_{126}$, $(I-3)_{130}$, $(I-3)_{134}$ and $(I-3)_{140}$, and, for example, Compound $(I-3)_3$ means a compound wherein $R^1$ is a hydroxyl group, $R^2$ is a methyl group and $(R^3)_n$ is 4—$OCHF_2$ in the compound represented by the formula (I)).

(Synthesis method 4)

The compound (I-4) (the compound (I) in which $R^1$ is a fluorine atom) can be synthesized generally by reacting the compound (I-3) and a fluorinating agent in the presence or absence of a solvent.

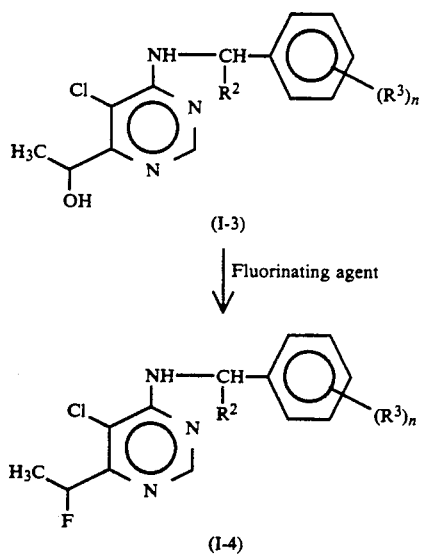

wherein $R^2$, $R^3$ and n each have the same meanings as defined above.

As the solvent, there may be mentioned the chlorinated or unchlorinated aromatic, aliphatic or alicyclic hydrocarbons, ethers and a mixture of the above solvents described in Synthesis method 1.

The solvent may be used in such an amount that the concentration of the compound (I-3) becomes 5 to 80% by weight, preferably in such an amount that the concentration of the compound (I-3) becomes 10 to 70% by weight.

As the fluorinating agent, there may be used diethylaminosulfur trifluoride (DAST) represented by the following formula:

The amount of the fluorinating agent to be used may be 1 to 5-fold mole, preferably 1 to 2-fold mole based on the amount of the compound (I-3).

The reaction temperature is not particularly limited, but may be in the temperature range of ice cooling temperature to a boiling point or lower of a solvent used, preferably room temperature to 40° C.

The reaction time varies depending on the above concentration and temperature, but may be generally 0.3 to 2 hours.

After completion of the reaction, the desired compound (I-4) prepared as described above may be subjected to conventional post-treatments such as extraction, condensation and filtration, and purified suitably by a known means such as recrystallization and various chromatographies, if necessary.

As the compound (I-4), there may be mentioned, for example, the respective compounds (I-4) comprising the respective kinds of substituents corresponding to Compounds 4, 11, 19, 48, 49, 54, 55, 59, 62, 64, 70, 71, 75, 79, 83, 88, 92, 96, 100, 102 to 111, 115 to 117, 121 to 123, 127 to 129, 131, 135 to 137 and 141 to 143 shown in Table 1 (referred to as Compounds $(I-4)_4$, $(I-4)_{11}$, $(I-4)_{19}$, $(I-4)_{48}$, $(I-4)_{49}$, $(I-4)_{54}$, $(I-4)_{55}$, $(I-4)_{59}$, $(I-4)_{62}$, $(I-4)_{64}$, $(I-4)_{70}$, $(I-4)_{71}$, $(I-4)_{75}$, $(I-4)_{79}$, $(I-4)_{83}$, $(I-4)_{88}$, $(I-4)_{92}$, $(I-4)_{96}$, $(I-4)_{100}$, $(I-4)_{102}$ to $(I-4)_{111}$, $(I-4)_{115}$ to $(I-4)_{117}$, $(I-4)_{121}$ to $(I-4)_{123}$, $(I-4)_{127}$ to $(I-4)_{129}$, $(I-4)_{131}$, $(I-4)_{135}$ to $(I-4)_{137}$ and $(I-4)_{141}$ to $(I-4)_{143}$, and, for example, Compound $(I-4)_4$ means a compound wherein $R^1$ is a fluorine atom, $R^2$ is a methyl group and $(R^3)_n$ is 4—$OCHF_2$ in the compound represented by the formula (I)).

(Synthesis method 5)

The compound (I-5) (the compound (I) in which $R^1$ is a lower alkoxy group or a lower alkylthio group) can be synthesized generally by reacting the compound (I-1) and the compound (VI) in the presence or absence of a solvent. In order to accelerate the reaction, the compounds are reacted preferably in the presence of a base.

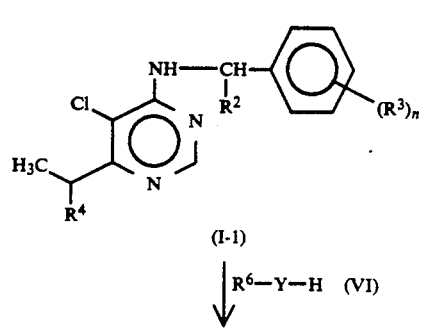

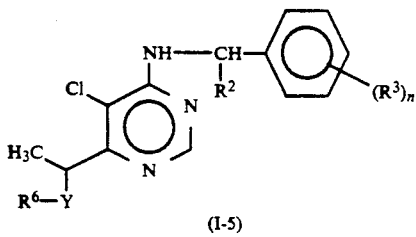

(I-5)

wherein $R^2$, $R^3$, $R^4$, $R^6$, Y and n each have the same meanings as defined above.

As the solvent, there may be mentioned the solvent described in Synthesis method 1.

The solvent may be used in such an amount that the concentration of the compound (I-1) becomes 5 to 80% by weight, preferably in such an amount that the concentration of the compound (I-1) becomes 10 to 70% by weight.

As the base, there may be mentioned the base described in synthesis method 1, and preferred are inorganic bases.

The amount of the base to be used may be 1 to 5-fold mole, preferably 1 to 3-fold mole based on the amount of the compound (I-1).

The reaction temperature is not particularly limited, but may be in the temperature range of room temperature to a boiling point or lower of a solvent used, preferably room temperature to 60° C.

The reaction time varies depending on the above concentration and temperature, but may be generally 0.3 to 2 hours.

The amount of the compound (VI) to be used may be 1 to 5-fold mole, preferably 1 to 2-fold mole based on the compound (I-1).

As the compound (VI), a commercially available product can be used.

After completion of the reaction, the desired compound (I-5) prepared as described above may be subjected to conventional post-treatments such as extraction, condensation and filtration, and purified suitably by a known means such as recrystallization and various chromatographies, if necessary.

As the compound (I-5), there may be mentioned, for example, the respective compounds (I-5) comprising the respective kinds of substituents corresponding to Compounds 6, 7, 13, 14, 21 and 22 shown in Table 1 (referred to as Compounds (I-5)$_6$, (I-5)$_7$, (I-5)$_{13}$, (I-5)$_{14}$, (I-5)$_{21}$ and (I-5)$_{22}$, and, for example, Compound (I-5)$_6$ means a compound wherein $R^1$ is a methoxy group, $R^2$ is a methyl group and $(R^3)_n$ is 4—OCHF$_2$ in the compound represented by the formula (I)).

(Synthesis method 6)

The compound (I-4) (the compound (I) in which $R^1$ is a fluorine atom) can be also synthesized by a method of reacting the compound (I-1) and the compound (VII) in the presence or absence of a solvent other than Synthesis method 4.

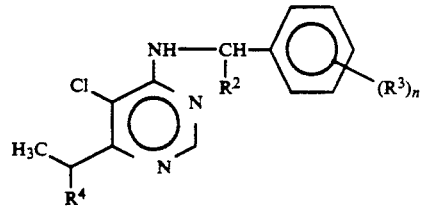

(I-1)

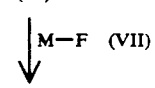

M—F (VII)

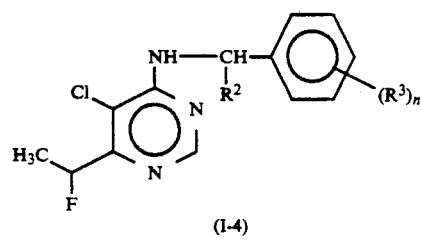

(I-4)

wherein $R^2$, $R^3$, $R^4$, M and n each have the same meanings as defined above.

As the solvent, there may be mentioned amide solvents such as N,N-dimethylformamide and N,N-dimethylacetamide, 1,3-dimethyl-2-imidazoline, dimethylsulfoxide, sulforane and a mixture of the above solvents. The solvent may be used in such an amount that the concentration of the compound (I-1) becomes 5 to 80% by weight, preferably in such an amount that the concentration of the compound (I-1) becomes 10 to 70% by weight.

As the compound (VII), there may be mentioned an alkali metal fluoride compound, and preferred are cesium fluoride and potassium fluoride.

The amount of the compound (VII) to be used may be 1 to 5-fold mole, preferably 1.2 to 3-fold mole based on the amount of the compound (I-1).

The reaction temperature is not particularly limited, but may be in the temperature range of room temperature to a boiling point or lower of a solvent used, preferably room temperature to 40° C.

The reaction time varies depending on the above concentration and temperature, but may be generally 1 to 8 hours.

After completion of the reaction, the desired compound (I-4) prepared as described above may be subjected to conventional post-treatments such as extraction, condensation and filtration, and purified suitably by a known means such as recrystallization and various chromatographies, if necessary.

As the compound (I-4), there may be mentioned the respective compounds described in Synthesis method 4.

As the noxious organisms on which controlling effect by the compound (I) of the present invention can be observed, there may be mentioned agricultural and horticultural noxious insects (e.g. Hemiptera (planthoppers, leafhoppers, aphides and whiteflies), Lepidoptera (cabbage armyworms, diamond-back moth, leafroller moths, pyralid moths and common cabbage worm), Coleoptera (Tenebrionid beetles, leafbeetles, weevils and scarabs) and Acarina (citrus red mite and two-spotted spider mite of Tetranychidae family and pink citrus rust mite of Eriophyidae family)), hygienically noxious insects (e.g. flies, mosquitos and cockroaches), noxious insects of stored grains (e.g. rust-red flour beetles and bean weevils), and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

The chemical for controlling noxious organisms of the present invention has remarkable insecticidal, acaricidal, nematocidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dust, an emulsifiable concentrate, a fine granule, a granule, a wettable powder, an oily suspension and an aerosol) according to a conventional method.

As the carrier, any insecticidally, acaricidally, nematocidally or fungicidally effective carrier may be used, and there may be mentioned, for example, a solid carrier such as talc, bentonite, clay, kaolin, diatomaceous earth, white carbon, vermiculite, calcium hydroxide, siliceous sand, ammonium sulfate and urea; a liquid carrier such as hydrocarbons (kerosine and mineral oil), aromatic hydrocarbons (benzene, toluene and xylene), chlorinated hydrocarbons (chloroform and carbon tetrachloride), ethers (dioxane and tetrahydrofuran), ketones (acetone, cyclohexanone and isophorone), esters (ethyl acetate, ethylene glycol acetate and dibutyl maleate), alcohols (methanol, n-hexanol and ethylene glycol), polar solvents (dimethylformamide and dimethylsulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dust, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Reference example and Examples, but the scope of the present invention is not limited by these Examples.

Reference example 1 (Syntheses of starting compounds (II))

(1) Synthesis of 6-(1-chloroethyl)-4,5-dichloropyrimidine (compound (II-1))

In 750 ml of dichloromethane was dissolved 270 g of 4,5-dichloro-6-ethylpyrimidine, and chlorine gas was blown into the mixture for 2 hours while heating to 30° to 35° C. and stirring.

Nitrogen gas was blown into the reaction mixture, and excessive chlorine gas dissolved in the mixture was removed. Subsequently, the solvent was removed under reduced pressure, and the resulting residue was evaporated under reduced pressure to obtain 240 g of the title compound as pale yellow liquid.

(2) Synthesis of 4,5-dichloro-6-(1-fluoroethyl)pyrimidine (compound (II-4))

In 15 ml of dichloromethane was dissolved 2.1 g of 6-(1-hydroxyethyl)-4,5-dichloropyrimidine, and to the mixture was added dropwise 2.0 g of diethylaminosulfur trifluoride under ice cooling and stirring. The mixture was further stirred for 1 hour at room temperature to complete the reaction.

To the reaction mixture was added 20 ml of cold water, and the dichloromethane layer was collected by separation, washed with water and dried over anhydrous sodium sulfate. Subsequently, the solvent was removed under reduced pressure, and the resulting residue was purified by column chromatography (Wako gel C-200 (trade name, manufactured by Wako Junyaku K.K.), eluted by chloroform) to obtain 1.3 g of the title compound as pale yellow oily liquid.

(Physical properties)

b.p.: 229° to 231° C.

$^1$H-NMR(CDCl$_3$) δppm 1.64 to 1.81 (d-d, 3H), 5.84 to 6.19 (d-q, 1H), 8.92 (s, 1H)

(3) Synthesis of 5-chloro-4-fluoro-6-(1-fluoroethyl)-pyrimidine (compound (II-5))

In 10 ml of N,N-dimethylformamide was dissolved 1.3 g of 4,5-dichloro-6-(1-fluoroethyl)pyrimidine, and to the mixture was added 4.0 g of cesium fluoride. The mixture was stirred at room temperature for 90 minutes to complete the reaction.

To the reaction mixture was added 10 ml of cold water, and the separated oily product was extracted with toluene, washed with water and dried over anhydrous sodium sulfate. Subsequently, the solvent was removed under reduced pressure, and the resulting residue was purified by column chromatography (Wako gel C-200 (trade name, manufactured by Wako Junyaku K.K.), eluted by chloroform) to obtain 1.0 g of the title compound as pale yellow oily liquid.

(Physical properties)

b p.: 192° to 194° C.

$^1$H-NMR(CDCl$_3$) δppm 1.66 to 1.82 (d-d, 3H), 5.85 to 6.21 (d-q, 1H), 8.83 (s, 1H)

(4) Synthesis of 6-(1-acetoxyethyl)-4,5-dichloropyrimidine (compound (II-6))

In 150 ml of N,N-dimethylformamide was dissolved 10.2 g of 6-(1-chloroethyl)-4,5-dichloropyrimidine, and to the mixture were added 12.0 g of potassium acetate and 3.0 g of potassium carbonate. The mixture was stirred at about 60° C. for 3 hours.

To the reaction mixture was added 200 ml of water, and the separated oily product was extracted with toluene, washed with water and dried over anhydrous sodium sulfate. Subsequently, the solvent was removed under reduced pressure, and the resulting residue was purified by column chromatography (Wako gel C-200 (trade name, manufactured by Wako Junyaku K.K.), eluted by toluene:ethyl acetate=10:1) to obtain 5.2 g of the title compound as pale yellow liquid.

(Physical properties)

$n_D^{17.1}$ 1.5222

$^1$H-NMR(CDCl$_3$) δppm 1.55 to 1.62 (d, 3H), 2.15 (s, 3H), 6.00 to 6.12 (q, 1H), 8.84 (s, 1H)

(5) Synthesis of 4,5-dichloro-6-(1-hydroxyethyl)pyrimidine (compound (II-7))

In 50 ml of tetrahydrofuran was dissolved 4.0 g of 6-(1-acetoxyethyl)-4,5-dichloropyrimidine, and to the mixture was slowly added dropwise 30 ml of an 1N-sodium hydroxide aqueous solution under stirring. After the dropwise addition, the mixture was further stirred for 1 hour at room temperature to complete the reaction.

Subsequently, the reaction mixture was extracted with ethyl acetate, washed with water and dried over anhydrous sodium sulfate. Then, the solvent was removed under reduced pressure, and the resulting oily product was purified by column chromatography (Wako gel C-200 (trade name, manufactured by Wako Junyaku K.K.), eluted by toluene:ethyl acetate=5:1) to obtain 2.8 g of the title compound as pale yellow liquid.

(Physical properties)

$n_D^{19.3}$ 1.5540

$^1$H-NMR(CDCl$_3$) δppm 1.47 to 1.52 (d, 3H), 3.76 to 3.85 (d, 1H), 5.17 to 5.25 (m, 1H), 8.88 (s, 1H)

(6) Syntheses of other starting compounds (II) in Table 3

The other starting compounds (II) in Table 3 were synthesized in the same manner as in the above (1) to (5).

Example 1 (Syntheses of compounds (I))

By using the starting compounds (II) obtained in Reference example 1, the title compounds (I) were synthesized.

(1) Synthesis of 5-chloro-6-(1-chloroethyl)-4-[1-(4-difluoromethoxyphenyl)ethylamino]pyrimidine (Compound 1)

In 50 ml of toluene were dissolved 3.8 g of 1-(4-difluoromethoxyphenyl)ethylamine and 2.3 g of triethylamine, and to the mixture was added 3.5 g of 6-(1-chloroethyl)-4,5-dichloropyrimidine. The mixture was refluxed under heating for 5 hours.

After completion of the reaction, the solvent was removed under reduced pressure, and the reaction mixture was extracted with ethyl acetate, washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene:ethyl acetate=9:1) to obtain 5.8 g of the title compound as colorless oily liquid.

(2) Synthesis of 6-(1-acetoxyethyl)-5-chloro-4-[1-(4-difluoromethoxyphenyl)ethylamino]pyrimidine (Compound 2)

In 50 ml of acetic acid was dissolved 3.1 g of 5-chloro-6-(1-chloroethyl)-4-[1-(4-difluoromethoxyphenyl)ethylamino]-pyrimidine, and to the mixture were added 3.0 g of potassium acetate and 3.0 g of potassium carbonate. The mixture was refluxed under heating for 30 hours.

After completion of the reaction, the solvent was removed under reduced pressure. Water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene:ethyl acetate=3:1) to obtain 2.7 g of the title compound as colorless oily liquid.

(3) Synthesis of 5-chloro-6-(1-hydroxyethyl)-4-[1-(4-difluoromethoxyphenyl)ethylamino]pyrimidine (Compound 3)

In 20 ml of an ethanol solution (mixture of ethanol and 10% sodium hydroxide aqueous solution at volume ratio of 1:1) was dissolved 2.0 g of 6-(1-acetoxyethyl)-5-chloro-4-[1-(4-difluoromethoxyphenyl)ethylamino]-pyrimidine, and the mixture was stirred at room temperature for 3 hours.

After completion of the reaction, ethanol was removed under reduced pressure, and the reaction mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene:ethyl acetate=1:1) to obtain 1.6 g of the title compound as colorless oily liquid.

(4) Synthesis of 5-chloro-6-(1-fluoroethyl)-4-[1-(4-difluoromethoxyphenyl)ethylamino]pyrimidine (Compound 4)

In 30 ml of dichloromethane was dissolved 1.0 g of 5-chloro-6-(1-hydroxyethyl)-4-[1-(4-difluoromethoxyphenyl)-ethylamino]pyrimidine, and to the mixture was added dropwise 0.4 g of diethylaminosulfur trifluoride under ice cooling. The mixture was stirred at room temperature for 1 hour.

After completion of the reaction, 30 ml of ice water was added to the reaction mixture, and the mixture was extracted with chloroform. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene:ethyl acetate=1:1) to obtain 0.6 g of the title compound as colorless oily liquid.

(5) Synthesis of 5-chloro-6-(1-methoxyethyl)-4-(1-phenylethylamino)pyrimidine (Compound 21)

In 20 ml of methanol was dissolved 1.11 g of 5-chloro-6-(1-chloroethyl)-4-(1-phenylethylamino)-pyrimidine, and to the mixture was added 1.3 g of a 28% sodium methoxide methanol solution. The mixture was stirred at 60° C. for 13 hours.

After completion of the reaction, the solvent was removed under reduced pressure. Water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene:ethyl acetate=10:1) to obtain 0.92 g of the title compound as colorless oily liquid.

(6) Synthesis of 5-chloro-6-(1-methylthioethyl)-4-(1-phenylethylamino)pyrimidine (Compound 22)

In 30 ml of methanol was dissolved 1.20 g of 5-chloro-6-(1-chloroethyl)-4-(1-phenylethylamino)-pyrimidine, and to the mixture was added 2.89 g of a methanethiol sodium salt 15% aqueous solution. The mixture was stirred at room temperature for 3 hours.

After completion of the reaction, the solvent was removed under reduced pressure. Water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene) to obtain 0.8 g of the title compound as colorless oily liquid.

(7) Synthesis of 4-benzylamino-5-chloro-6-(1-fluoroethyl)pyrimidine (Compound 48)

In 30 ml of N,N-dimethylformamide was dissolved 2.8 g of 4-benzylamino-5-chloro-6-(1-chloroethyl)-pyrimidine, and to the mixture was added 3.0 g of cesium fluoride. The mixture was stirred at 120° to 140° C. for 12 hours.

After completion of the reaction, water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=9:1) to obtain 1.3 g of the title compound as colorless oily liquid.

(8) Synthesis of 5-chloro-6-(1-fluoroethyl)-4-[1-(4-chlorophenyl)cyclopropylmethylamino]pyrimidine (Compound 83)

In 30 ml of toluene were dissolved 1.8 g of 1-(4-chlorophenyl)cyclopropylmethylamine and 1.3 g of triethylamine, and to the mixture was added 2.0 g of 4,5-dichloro-6-(1-fluoroethyl)pyrimidine under stirring. The mixture was refluxed under heating for 5 hours.

After completion of the reaction, water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=8:1) to obtain 1.8 g of the title compound as colorless oily liquid.

(9) Synthesis of 5-chloro-6-(1-hydroxyethyl)-4-[1-(4-trifluoromethoxyphenyl)ethylamino]pyrimidine (Compound 87)

In 30 ml of toluene were dissolved 2.1 g of 4-[1-(4-trifluoromethoxyphenyl)ethylamine and 1.3 g of triethylamine, and to the mixture was added 2.0 g of 4,5-dichloro-6-(1-hydroxyethyl)pyrimidine under stirring. The mixture was refluxed under heating for 5 hours.

After completion of the reaction, water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=10:1) to obtain 2.4 g of the title compound as colorless oily liquid.

(10) Synthesis of 6-(1-acetoxyethyl)-5-chloro-4-[1-(4-methylthiophenyl)ethylamino]pyrimidine (Compound 98)

In 30 ml of toluene were dissolved 1.8 g of 1-(4-methylthiophenyl)ethylamine and 1.3 g of triethylamine, and to the mixture was added 2.4 g of 6-(1-acetoxyethyl)-4,5-dichloropyrimidine under stirring. The mixture was refluxed under heating for 5 hours.

After completion of the reaction, water was added to the reaction mixture, and the mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=10:1) to obtain 2.8 g of the title compound as colorless oily liquid.

(11) Synthesis of 5-chloro-6-(1-hydroxyethyl)-4-[1-(4-methylthiophenyl)ethylamino]pyrimidine (Compound 99)

In 100 ml of an ethanol solution (mixture of ethanol and 10% sodium hydroxide aqueous solution at volume ratio of 1:1) was dissolved 5.5 g of 6-(1-acetoxyethyl)-5-chloro-4-[1-(4-methylthiophenyl)ethylamino]pyrimidine, and the mixture was stirred at room temperature for 3 hours.

After completion of the reaction, ethanol was removed under reduced pressure, and the reaction mixture was extracted with ethyl acetate. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=1:1) to obtain 4.7 g of the title compound as colorless crystal.

(12) Synthesis of 5-chloro-6-(1-fluoroethyl)-4-[1-(4-methylthiophenyl)ethylamino]pyrimidine (Compound 100)

In 80 ml of dichloromethane was dissolved 4.7 g of 5-chloro-6-(1-hydroxyethyl)-4-[1-(4-methylthiophenyl)ethylamino]pyrimidine, and to the mixture was added dropwise 2.6 g of diethylaminosulfur trifluoride under ice cooling. The mixture was stirred at room temperature for 1 hour.

After completion of the reaction, 30 ml of ice water was added to the reaction mixture, and the mixture was extracted with chloroform. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by toluene-:ethyl acetate=10:1) to obtain 3.8 g of the title compound as a pale yellow oily product.

(13) Syntheses of 5-chloro-6-(1-fluoroethyl)-4-[1-(4-methylsulfinylphenyl)ethylamino]pyrimidine (Compound 103) and 5-chloro-6-(1-fluoroethyl)-4-[1-(4-methylsulfonylphenyl)ethylamino]pyrimidine (Compound 104)

In 50 ml of dichloromethane was dissolved 2.6 g of 5-chloro-6-(1-fluoroethyl)-4-[1-(4-methylthiophenyl)ethylamino] pyrimidine, and to the mixture was added 1.6 g of metachloroperbenzoic acid. The mixture was stirred at room temperature for 1 hour.

After completion of the reaction, a saturated sodium hydrogen carbonate aqueous solution was added to the reaction mixture, and the mixture was extracted with chloroform. The extract was washed with water and dried over anhydrous sodium sulfate, and the solvent was removed under reduced pressure.

The resulting oily product was purified by column chromatography (Wako gel C-200 (trade name, manufactured by Wako Junyaku K.K.), eluted by ethyl acetate) to obtain 0.8 g of the title compound (Compound 104) as colorless crystal and 1.4 g of the title compound (Compound 103) as a colorless rubber-like product.

(14) Syntheses of other title compounds (I)

The other title compounds (I) shown in Table 1 were synthesized according to the methods as described in the above (1) to (13).

Example 2 (Preparation of formulations)

(1) Preparation of granule

Five parts by weight of Compound 1 was uniformly mixed with 35 parts by weight of bentonite, 57 parts by weight of talc, 1 part by weight of Neopelex powder (trade name, produced by Kao K.K.) and 2 parts by weight of sodium lignosulfonate, and then, the mixture was kneaded with addition of a small amount of water, followed by granulation and drying, to obtain a granule.

(2) Preparation of wettable powder

Ten parts by weight of Compound 1 was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of emulsifiable concentrate

Twenty parts by weight of Compound 1 was uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dust

Five parts by weight of Compound 1 was uniformly mixed with 50 parts by weight of talc and 45 parts by weight of kaolin to obtain a dust.

Example 3 (Tests of effects)

(1) Test of effect on common cutworm

The respective wettable powders of the compounds (I) shown in Table 1 prepared as in Example 2 were diluted to 500 ppm with water containing a surfactant (0.01%). In these respective chemicals, soy bean main leaves were dipped for 30 seconds, respectively, and one leaf was put into a plastic cup and air-dried.

Subsequently, 10 common cutworms (2nd instar larvae) were placed in the respective cups. The cups were closed with caps and left to stand in a thermostat chamber at 25° C. After 2 days, insecticidal rate was determined by counting living and dead insects in the respective cups.

For comparison, the compound represented by the following formula:

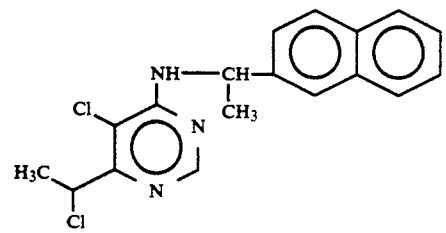

described in European Patent Publication No. 470 600 (corresponding to Japanese Provisional Patent Publication No. 230670/1992) was made into a formulation in the same manner as in the compound of the present invention, and the same experiment was conducted.

The insecticidal effect was evaluated by using 4 ranks depending on the range of insecticidal rate (A: 100%, B: 99 to 80%, C: 79 to 60% and D: 59% or less). These results are shown in Table 4.

TABLE 4

| Test of effect on common cutworm | |
|---|---|
| Compound | Effect |
| 4 | A |
| 75 | A |
| 105 | A |
| (X) | D |

(2) Test of effect on brown rice planthopper

The respective wettable powders of the compound (I) shown in Table 1 prepared as in Example 2 were diluted to 300 ppm with water containing a surfactant (0.01%). In these respective chemicals, young seedlings of rice were dipped for 30 seconds, respectively, air-dried and put into the respective glass cylinders.

Subsequently, 10 brown rice planthoppers (4th instar nymphs) were placed in the respective glass cylinders. The cylinders were closed with porous caps and left to stand in a thermostat chamber at 25° C. After 4 days, insecticidal rate was determined by counting living and dead insects in the respective glass cylinders.

The evaluation results of the insecticidal effects of the present compounds and the compound (X) for comparison described in the above (1) are shown in Table 5 according to the 4 rank evaluation method.

TABLE 5

| Test of effect on brown rice planthopper | |
|---|---|
| Compound | Effect |
| 4 | A |
| 11 | A |
| 19 | A |
| 59 | A |
| 64 | A |
| 70 | A |
| 71 | B |
| 75 | A |
| 79 | A |
| 83 | B |
| 88 | A |
| 96 | A |
| 105 | A |
| 106 | B |
| 107 | A |
| 108 | A |
| 109 | A |
| 121 | B |
| 135 | B |
| (X) | D |

(3) Test of effect on two-spotted spider mite female adult

The respective wettable powders of the compounds (I) shown in Table 1 prepared as in Example 2 were diluted to 300 ppm with water containing a surfactant (0.01%), and in these respective chemicals, kidney bean leaves (diameter: 20 mm) on which 10 two-spotted spider mite female adults were parasitic were dipped for 10 seconds, respectively.

Subsequently, these respective leaves were left to stand in a thermostat chamber at 25° C., and after 3 days, acaricidal rate was determined by counting living and dead mites in the respective leaves.

The evaluation results of the acaricidal effects of the present compounds and the compound (X) for comparison described in the above (1) are shown in Table 6 according to the 4 rank evaluation method.

TABLE 6

Test of effect on two-spotted spider mite

| Compound | Effect |
| --- | --- |
| 1 | A |
| 4 | A |
| 8 | A |
| 11 | A |
| 19 | B |
| 59 | A |
| 64 | B |
| 70 | A |
| 71 | A |
| 74 | B |
| 76 | B |
| 79 | A |
| 83 | A |
| 84 | A |
| 85 | A |
| 88 | A |
| 92 | A |
| 96 | A |
| 100 | A |
| 105 | A |
| 106 | A |
| 107 | A |
| 108 | B |
| 109 | A |
| 115 | A |
| 120 | B |
| 121 | A |
| 127 | A |
| 135 | A |
| (X) | D |

(4) Test of effect on southern root-know nematode

The respective wettable powders of the compounds (I) shown in Table 1 prepared as in Example 2 were diluted to 20 ppm with water, and 0.5 ml of each chemical obtained and 0.5 ml of an aqueous solution having 30 to 40 southern root-knot nematode secondary larvae (within 24 hours after hatching) were charged in a test tube.

Subsequently, the test tubes were left to stand in a thermostat chamber at 25° C., and after 2 days, nematocidal rate was determined by counting living and dead nematodes with a microscope (40 magnifications).

The nematocidal effect was evaluated by using 4 ranks depending on the range of nematocidal rate (A: 100 to 90%, B: 89 to 80%, C: 79 to 60% and D: 59% or less).

The evaluation results of the nematocidal effects of the present compounds and the compound (X) for comparison described in the above (1) are shown in Table 7.

TABLE 7

Test of effect on southern root-knot nematode

| Compound | Effect |
| --- | --- |
| 1 | B |
| 4 | A |
| 9 | B |
| 11 | A |
| 49 | B |
| 55 | B |
| 59 | A |
| 71 | A |
| 72 | B |
| 75 | A |
| 79 | A |
| 83 | A |
| 85 | B |
| 88 | A |
| 92 | A |
| 96 | A |
| 100 | A |
| 102 | A |
| 103 | A |
| 104 | A |
| 105 | A |
| 106 | A |
| 107 | A |
| 108 | A |
| 115 | A |
| 116 | B |
| 117 | A |
| 121 | A |
| 135 | A |
| 136 | A |
| 137 | A |
| 141 | A |
| 142 | A |
| 143 | A |
| (X) | D |

(5) Test of controlling effect on powdery mildew (barley) (prevention effect)

In plastic flowerpots having a diameter of 6 cm, 10 barleys (variety: Kuromugi) were grown per one flowerpot, and to the young plants at 1.5 leaf stage, the chemicals obtained by diluting the wettable powders of the compounds (I) shown in Table 1 prepared as in Example 2 to 500 ppm with water containing a surfactant (0.01%) were sprayed in an amount of 20 ml per one flowerpot, respectively.

These barleys were grown in a glass greenhouse for 2 days, and then conidiospores of powdery mildew (barley) collected from infected leaves were dusted uniformly over the respective plants to be inoculated thereinto.

Then, these plants were grown in a glass greenhouse for one week, and the degree of lesion of powdery mildew (barley) appeared on the respective first leaves was examined.

The fungicidal effect was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

These results are shown in Table 8.

TABLE 8

Test of controlling effect on powdery mildew (barley) (prevention effect)

| Compound | Effect |
| --- | --- |
| 1 | 5 |
| 2 | 5 |
| 4 | 5 |
| 8 | 5 |

TABLE 8-continued

Test of controlling effect on powdery mildew (barley) (prevention effect)

| Compound | Effect |
|---|---|
| 9 | 4 |
| 10 | 5 |
| 11 | 5 |
| 15 | 5 |
| 19 | 5 |
| 23 | 4 |
| 27 | 4 |
| 30 | 4 |
| 33 | 5 |
| 34 | 5 |
| 35 | 5 |
| 37 | 4 |
| 38 | 4 |
| 40 | 5 |
| 41 | 5 |
| 43 | 5 |
| 48 | 5 |
| 49 | 5 |
| 50 | 5 |
| 51 | 4 |
| 54 | 5 |
| 55 | 5 |
| 59 | 5 |
| 64 | 5 |
| 65 | 4 |
| 66 | 4 |
| 67 | 4 |
| 68 | 5 |
| 69 | 5 |
| 70 | 5 |
| 71 | 5 |
| 72 | 4 |
| 73 | 4 |
| 74 | 4 |
| 75 | 4 |
| 79 | 4 |
| 83 | 5 |
| 86 | 5 |
| 87 | 5 |
| 88 | 5 |
| 92 | 5 |
| 96 | 5 |
| 100 | 5 |
| 104 | 5 |
| 105 | 5 |
| 106 | 5 |
| 107 | 5 |
| 108 | 5 |
| 109 | 5 |
| 110 | 5 |
| 111 | 5 |
| 115 | 5 |
| 117 | 5 |
| 121 | 5 |
| 123 | 5 |
| 129 | 5 |
| 135 | 5 |
| 137 | 5 |
| 141 | 5 |
| 143 | 5 |
| Non-treated district | 0 |

(6) Test for controlling effect on brown rust (wheat) (prevention effect)

In plastic flowerpots having a diameter of 6 cm, 10 wheats (variety: Kobushi wheat) were grown per one flowerpot, and to the young plants at 1.5 leaf stage, the chemicals obtained by diluting the wettable powders of the compounds (I) shown in Table 1 prepared as in Example 2 to 500 ppm with water containing a surfactant (0.01%) were sprayed in an amount of 20 ml per one flowerpot, respectively. After spraying, the wheats were grown in a glass greenhouse for 2 days, and then a suspension of spores of brown rust (wheat) ($7 \times 10^4$/ml) was sprayed uniformly to the plants to be inoculated thereinto.

After inoculation, the wheats were grown in a glass greenhouse for one week, and the degree of lesion of brown rust (wheat) appeared on the first leaves was examined.

The results are shown in Table 9 according to the 6 rank evaluation method described in the above (5).

TABLE 9

Test of controlling effect on brown rust (wheat) (prevention effect)

| Compound | Effect |
|---|---|
| 1 | 5 |
| 3 | 4 |
| 4 | 4 |
| 8 | 5 |
| 9 | 4 |
| 10 | 5 |
| 11 | 5 |
| 15 | 5 |
| 16 | 4 |
| 18 | 5 |
| 19 | 5 |
| 21 | 5 |
| 22 | 5 |
| 23 | 5 |
| 25 | 4 |
| 27 | 5 |
| 33 | 5 |
| 34 | 5 |
| 35 | 5 |
| 48 | 5 |
| 49 | 5 |
| 52 | 4 |
| 53 | 4 |
| 54 | 5 |
| 55 | 5 |
| 56 | 4 |
| 59 | 5 |
| 63 | 5 |
| 64 | 5 |
| 66 | 4 |
| 67 | 5 |
| 68 | 4 |
| 69 | 5 |
| 70 | 5 |
| 71 | 5 |
| 73 | 4 |
| 74 | 4 |
| 75 | 5 |
| 76 | 5 |
| 77 | 5 |
| 78 | 5 |
| 79 | 5 |
| 83 | 5 |
| 86 | 5 |
| 87 | 5 |
| 88 | 5 |
| 91 | 5 |
| 92 | 5 |
| 96 | 5 |
| 100 | 5 |
| 105 | 5 |
| 106 | 5 |
| 107 | 5 |
| 108 | 5 |
| 109 | 5 |
| 110 | 5 |
| 111 | 5 |
| 115 | 5 |
| 121 | 5 |
| 135 | 5 |
| 141 | 5 |
| Non-treated district | 0 |

The novel aralkylaminopyrimidine derivative of the present invention is an useful agricultural chemical having an excellent effect of controlling noxious organisms such as insecticidal, acaricidal, nematocidal and fungicidal effects.

We claim:

1. An aralkylaminopyrimidine compound represented by the following formula:

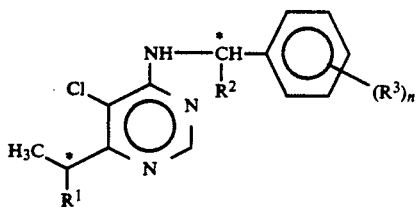

(I)

wherein $R^1$ represents a halogen atom, a lower acyloxy group, a hydroxyl group, a lower alkoxy group or a lower alkylthio group; $R^2$ represents a lower alkyl group, a hydrogen atom or a cycloalkyl group; $R^3$ may be the same or different and represents a lower haloalkoxy group, a hydrogen atom, a lower alkyl group, a lower alkoxy group, a halogen atom, a lower alkylthio group, a nitro group, a lower haloalkyl group, a lower alkylsulfinyl group, a lower alkylsulfonyl group, a lower haloalkylthio group or a hydroxyl group; a carbon atom to which * is attached represents an asymmetric carbon atom provided that the case where $R^2$ is a hydrogen atom is excluded; and n represents an integer of 1 to 5.

2. The compound according to claim 1, wherein $R^1$ is a halogen atom, an acyloxy group having 2 to 6 carbon atoms, a hydroxyl group, an alkoxy group having 1 to 6 carbon atoms or an alkylthio group having 1 to 6 carbon atoms, $R^2$ is an alkyl group having 1 to 6 carbon atoms, a hydrogen atom or a cycloalkyl group having 3 to 8 carbon atoms, and $R^3$ is a haloalkoxy group having 1 to 6 carbon atoms, a hydrogen atom, an alkyl group having 1 to 6 carbon atoms, an alkoxy group having 1 to 6 carbon atoms, a halogen atom, an alkylthio group having 1 to 6 carbon atoms, a nitro group, an haloalkyl group having 1 to 6 carbon atoms, an alkylsulfinyl group having 1 to 6 carbon atoms, an alkylsulfonyl group having 1 to 6 carbon atoms, an haloalkylthio group having 1 to 6 carbon atoms or a hydroxyl group.

3. The compound according to claim 1, wherein $R^1$ is a chlorine atom, a fluorine atom, an acetyloxy group, a propionyloxy group, a hydroxyl group, a methoxy group or a methylthio group.

4. The compound according to claim 1, wherein $R^2$ is a methyl group, an ethyl group, an n-propyl group, a hydrogen atom or a cyclopropyl group.

5. The compound according to claim 1, wherein $R^3$ is a difluoromethoxy group, a trifluoromethoxy group, a hydrogen atom, a methyl group, a t-butyl group, a methoxy group, a chlorine atom, a fluorine atom, a bromine atom, a methylthio group, an ethylthio group, an n-propylthio group, an n-butylthio group, a difluoromethylthio group, a nitro group, a trifluoromethyl group, a methylsulfinyl group, an ethylsulfinyl group, an n-propylsulfinyl group, an n-butylsulfinyl group, a methylsulfonyl group, an ethylsulfonyl group, an n-propylsulfonyl group, an n-butylsulfonyl group or a hydroxyl group.

6. The compound according to claim 1, wherein $R^1$ is F, Cl, Br, OH, —OCH$_3$, —SCH$_3$ or —OCOCH$_3$, $R^2$ is H, CH$_3$, C$_2$H$_5$, C$_3$H$_7$ or cyclopropyl, and $R^3$ is H, CH$_3$, t-C$_4$H$_9$, Cl, F, Br, OCH$_3$, OCHF$_2$, NO$_2$, CF$_3$, OCF$_3$, SCH$_3$, SOCH$_3$, SO$_2$CH$_3$, SCHF$_2$, SCH$_2$CH$_3$, SOCH$_2$CH$_3$, SO$_2$CH$_2$CH$_3$, SCH$_2$CH$_2$CH$_3$, SOCH$_2$CH$_2$CH$_3$, SO$_2$CH$_2$CH$_2$CH$_3$, SCH$_2$CH$_2$CH$_2$CH$_3$, SOCH$_2$CH$_2$CH$_2$CH$_3$ or SO$_2$CH$_2$CH$_2$CH$_2$CH$_3$.

7. The compound according to claim 1, wherein said compound is 5-chloro-6-(1-chloroethyl)-4-[1-(4-difluoromethoxyphenyl)ethylamino]pyrimidine, 6-(1-acetoxyethyl)-5-chloro-4-[1-(4-difluoromethoxyphenyl)ethylamino]pyrimidine, 5-chloro-6-(1-hydroxyethyl)-4-[1-(4-difluoromethoxyphenyl)-ethylamino]pyrimidine, 5-chloro-6-(1-fluoroethyl)-4-[1-(4-difluoromethoxyphenyl)ethylamino]pyrimidine, 5-chloro-6-(1-methoxyethyl)-4-(1-phenylethylamino)pyrimidine, 5-chloro-6-(1-methylthioethyl)-4-(1-phenylethylamino)pyrimidine, 4-benzylamino-5-chloro-6-(1-fluoroethyl)pyrimidine, 5-chloro-6-(1-fluoroethyl)-4-[1-(4-chlorophenyl)cyclopropylmethylamino]pyrimidine, 5-chloro-6-(1-hydroxyethyl)-4-[1(4-trifluoromethoxyphenyl)ethylamino]pyrimidine, 6-(1-acetoxyethyl)-5-chloro-4-[1-(4-methylthiophenyl)ethylamino]-pyrimidine, 5-chloro-6-(1-hydroxyethyl)-4-[1-(4-methylthiophenyl)ethylamino]pyrimidine, 5-chloro-6-(1-fluoroethyl)-4-[1-(4-methylthiophenyl)ethylamino]pyrimidine, 5-chloro-6-(1-fluoroethyl)-4-[1-(4-methylsulfinylphenyl)ethylamino]pyrimidine, 5-chloro-6-(1-fluoroethyl)-4-[1-(4-methylsulfonylphenyl)ethylamino]pyrimidine, 5-chloro-6-(1-fluoroethyl)-4-[1-(4-difluoromethoxyphenyl)-propylamino]pyrimidine, 5-chloro-6-(1-fluoroethyl)-4-(1-phenylethylamino)pyrimidine, 5-chloro-6-(1-fluoroethyl)-4-(4-chlorobenzylamino)pyrimidine, 5-chloro-6-(1-fluoroethyl)-4-(4-methylbenzylamino)pyrimidine, 5-chloro-6-(1-fluoroethyl)-4-(4-methoxybenzylamino)pyrimidine, 5-chloro-6-(1-fluoroethyl)-4-[1-(4-methoxyphenyl)ethylamino]pyrimidine, 5-chloro-6-(1-fluoroethyl)-4-(1-phenylpropylamino)pyrimidine, 5-chloro-6-(1-fluoroethyl)-4-[1-(4-methylphenyl)propylamino]pyrimidine, 5-chloro-6-(1-fluoroethyl)-4-[1-(4-bromophenyl)propylamino]pyrimidine, 5-chloro-6-(1-fluoroethyl)-4-[1-(3-trifluoromethylphenyl)ethylamino]pyrimidine, 5-chloro-6-(1-fluoroethyl)-4-[1-(4-fluorophenyl)-propylamino]pyrimidine, 5-chloro-6-(1-fluoroethyl)-4-[1-(4-trifluoromethoxyphenyl)-ethylamino]pyrimidine, 5-chloro-6-(1-fluoroethyl)-4-[1-(3-chlorophenyl)ethylamino]pyrimidine, 5-chloro-6-(1-fluoroethyl)-4-[1-(3-bromophenyl)ethylamino]pyrimidine, 5-chloro-6-(1-fluoroethyl)-4-[1-(4-nitrophenyl)ethylamino]pyrimidine, 5-chloro-6-(1-fluoroethyl)-4-[1-(4-difluoromethylthiophenyl)ethylamino]pyrimidine, 5-chloro-6-(1-fluoroethyl)-4-[1-(3-difluoromethoxyphenyl)ethylamino]pyrimidine, 5-chloro-6-(1-fluoroethyl)-4-[1-(3-chloro-4-difluoromethoxyphenyl)ethylamino]pyrimidine, 5-chloro-6-(1-fluoroethyl)-4-[1-(4-difluoromethoxy-3-methoxyphenyl)ethylamino]pyrimidine, 5-chloro-6-(1-fluoroethyl)-4-[1-(4-difluoromethoxy-3,5-dimethylphenyl)ethylamino]pyrimidine, 5-chloro-6-(1-fluoroethyl)-4-[1-(3,4-dimethoxyphenyl)ethylamino]-pyrimidine, 5-chloro-6-(1-fluoroethyl)-4-[1-(2,5-dimethoxypheynl)ethylamino]pyrimidine, 5-chloro-6-(1-fluoroethyl)-4-[1-(4-ethylthiophenyl)ethylamino]pyrimidine, 5-chloro-6-(1-fluoroethyl)-4-[1-(4-ethylsulfinylphenyl)ethylamino]pyrimidine, 5-chloro-6-(1-fluoroethyl)-4-[1-(4-ethylsulfonylphenyl)ethylamino]pyrimidine, 5-chloro-6-(1-fluoroethyl)-4-[1-(4-n-propylthiophenyl)ethylamino]pyrimidine, 5-chloro-6-(1-fluoroethyl)-4-[1-(4-n-propylsulfinylphenyl)ethylamino]-pyrimidine, 5-chloro-6-(1- fluoroethyl)-4-[1-(4-n-propylsulfonylphenyl)ethylamino]pyrimidine, 5-chloro-6-(1-fluoroethyl)-4-[1-(4-n-butylthiophenyl)ethylamino]pyrimidine, 5-chloro-6-(1-fluoroethyl)-4-[1-(4-n-butylsulfinylphenyl)ethylamino]pyrimidine, 5-chloro-6-(1-fluoroethyl)-4-[1-(4-n-butylsulfonylphenyl)ethylamino]pyrimidine, 5-chloro-6-(1-fluoroethyl)-4-[1-(4-hydroxyphenyl)ethylamino]pyrimidine, 5-chloro-6-(1-fluoroethyl)-4-[1-(4-methylthiophenyl)propylamino]pyrimidine, 5-chloro-6-(1-fluoroethyl)-4-[1-(4-methylsulfinylphenyl)propylamino]pyridimine, 5-chloro-6-(1-fluoroethyl)-4-[1-(4-ethylsulfonylphenyl)propylamino]-pyrimidine, 5-chloro-6-(1-fluoroethyl)-4-[1-(4-methylthiophenyl)cyclopropylmethylamino]pyrimidine, 5-chloro-6-(1-fluoroethyl)-4-[1-(4-methylsulfinylphenyl)cyclopropylmethylamino]pyrimidine or 5-chloro-6-(1-fluoroethyl)-4-[1-(4-methylsulfonylphenyl)cyclopropylmethylamino]pyrimidine.

8. A composition for controlling noxious organisms comprising the aralkylaminopyrimidine compound represented by the formula (I) according to claim 1 as an active ingredient and an insecticidally, acaricidally, nematocidally or fungicidally effective carrier.

* * * * *

UNITED STATES PATENT AND TRADEMARK OFFICE
CERTIFICATE OF CORRECTION

PATENT NO.  : 5,280,025
DATED       : January 18, 1994
INVENTOR(S) : Tokio OBATA et al.

It is certified that error appears in the above-identified patent and that said Letters Patent is hereby corrected as shown below:

In the Abstract, line 18 of text, delete "a" and insert --A--.

Signed and Sealed this

Thirteenth Day of December, 1994

Attest:

BRUCE LEHMAN

*Attesting Officer*    *Commissioner of Patents and Trademarks*